US009828624B2

(12) United States Patent
Schaefer

(10) Patent No.: US 9,828,624 B2
(45) Date of Patent: Nov. 28, 2017

(54) DRIVING PATIENT COMPLIANCE WITH THERAPY

(71) Applicant: Boston Heart Diagnostics Corporation, Framingham, MA (US)

(72) Inventor: Ernst J. Schaefer, Natick, MA (US)

(73) Assignee: BOSTON HEART DIAGNOSTICS CORPORATION, Framingham, MA (US)

( * ) Notice: Subject to any disclaimer, the term of this patent is extended or adjusted under 35 U.S.C. 154(b) by 0 days.

(21) Appl. No.: 13/949,847

(22) Filed: Jul. 24, 2013

(65) Prior Publication Data

US 2015/0031058 A1    Jan. 29, 2015

(51) Int. Cl.
| | | |
|---|---|---|
| C12Q 1/60 | (2006.01) | |
| G01N 33/92 | (2006.01) | |
| G01N 33/50 | (2006.01) | |
| A61K 31/366 | (2006.01) | |
| A61K 31/40 | (2006.01) | |
| A61K 31/397 | (2006.01) | |

(52) U.S. Cl.
CPC ............ *C12Q 1/60* (2013.01); *G01N 33/5008* (2013.01); *G01N 33/92* (2013.01); *A61K 31/366* (2013.01); *A61K 31/397* (2013.01); *A61K 31/40* (2013.01)

(58) Field of Classification Search
CPC .............. A61K 2300/00; A61K 31/397; A61K 31/575; A61K 31/33
See application file for complete search history.

(56) References Cited

U.S. PATENT DOCUMENTS

| | | | |
|---|---|---|---|
| 3,703,591 | A | 11/1972 | Bucolo |
| 4,245,041 | A | 1/1981 | Denney |
| 4,330,299 | A | 5/1982 | Cerami |
| 4,495,279 | A | 1/1985 | Karpetsky et al. |
| 4,683,195 | A | 7/1987 | Mullis et al. |
| 4,683,202 | A | 7/1987 | Mullis |
| 4,800,159 | A | 1/1989 | Mullis et al. |
| 4,999,289 | A | 3/1991 | Akiba et al. |
| 5,223,392 | A | 6/1993 | Cohen |
| 5,436,149 | A | 7/1995 | Barnes |
| 5,843,663 | A | 12/1998 | Stanley et al. |
| 5,849,481 | A | 12/1998 | Urdea et al. |
| 5,849,486 | A | 12/1998 | Heller et al. |
| 5,851,772 | A | 12/1998 | Mirzabekov et al. |
| 5,888,827 | A | 3/1999 | Kayahara et al. |
| 5,900,481 | A | 5/1999 | Lough et al. |
| 5,919,626 | A | 7/1999 | Shi et al. |
| 5,955,351 | A | 9/1999 | Gerdes et al. |
| 6,194,164 | B1 | 2/2001 | Matsui et al. |
| 6,316,196 | B1 | 11/2001 | Morten |
| 6,410,309 | B1 | 6/2002 | Barbera-Guillem et al. |
| 6,582,908 | B2 | 6/2003 | Fodor et al. |
| 7,417,039 | B2 | 8/2008 | Davis |
| 7,435,541 | B2 | 10/2008 | Olson et al. |
| 7,608,405 | B2 | 10/2009 | Ebinuma et al. |
| 7,659,107 | B2 | 2/2010 | Smith et al. |
| 7,700,277 | B2 | 4/2010 | Ambrose et al. |
| 7,871,789 | B2 | 1/2011 | Yonehara et al. |
| 8,003,795 | B2 | 8/2011 | Liu et al. |
| 8,026,345 | B2 | 9/2011 | Burghardt et al. |
| 8,093,222 | B2 | 1/2012 | Freier et al. |
| 8,137,977 | B2 * | 3/2012 | Kaddurah-Daouk .. G01N 33/92 435/11 |
| 8,470,541 | B1 | 6/2013 | Asztalos et al. |
| 2003/0143223 | A1 | 7/2003 | Cabezas et al. |
| 2004/0131658 | A1 | 7/2004 | Kaput |
| 2004/0259179 | A1 | 12/2004 | Assmann et al. |
| 2005/0054005 | A1 | 3/2005 | Ellis et al. |
| 2005/0059581 | A1 | 3/2005 | Mantzoros |
| 2005/0281868 | A1 | 12/2005 | Lane |
| 2006/0293225 | A1 | 12/2006 | Dialynas et al. |

(Continued)

FOREIGN PATENT DOCUMENTS

| | | |
|---|---|---|
| EP | 1186672 A2 | 3/2002 |
| EP | 1651774 B1 | 9/2007 |

(Continued)

OTHER PUBLICATIONS

Jones PH, Davidson MH, Stein EA, et al. Comparison of the efficacy and safety of rosuvastatin versus atorvastatin, simvastatin, and pravastatin across doses (STELLAR* Trial). Am J Cardiol 2003;92:152-60.

Weng TC, Yang YH, Lin SJ, Tai SH. A systematic review and meta-analysis on the therapeutic equivalence of statins. J Clin Pharm Ther 2010;35:139-51.

Third Report of the National Cholesterol Education Program (NCEP) Expert Panel on Detection, Evaluation, and Treatment of High Blood Cholesterol in Adults (Adult Treatment Panel III) final report. (Divided into four parts).

Grundy SM, Cleeman JI, Merz CN, et al. Implications of recent clinical trials for the National Cholesterol Education Program Adult Treatment Panel III guidelines. Circulation 2004;110:227-39.

Catapano AL, Reiner Z, De Backer G, et al. ESC/EAS Guidelines for the management of dyslipidaemias the Task Force for the management of dyslipidaemias of the European Society of Cardiology (ESC) and the European Atherosclerosis Society (EAS). Atherosclerosis 2011;217:3-46.

(Continued)

*Primary Examiner* — Jennifer McDonald
*Assistant Examiner* — Qing Xu
(74) *Attorney, Agent, or Firm* — Brown Rudnick LLP; Thomas C. Meyers

(57) ABSTRACT

Methods of the invention involve determining a patient's compliance with a cholesterol lowering therapy. In certain aspects, the invention provides methods that involve conducting a first assay to determine a cholesterol biomarker level in a first sample from a patient prior to the patient undergoing a cholesterol lowering therapy. The methods may also involve conducting a second assay to determine a cholesterol level in a second sample obtained from the patient after the patient has started undergoing a cholesterol lowering therapy. Additionally, the methods involve associating the cholesterol level and the cholesterol biomarker level in which the association allows for the determination of the patient's compliance with the cholesterol lowering therapy.

9 Claims, No Drawings

(56) References Cited

U.S. PATENT DOCUMENTS

| | | |
|---|---|---|
| 2007/0003600 A1 | 1/2007 | Moore et al. |
| 2007/0015291 A1 | 1/2007 | Smith |
| 2007/0031838 A1 | 2/2007 | Ambrose et al. |
| 2007/0059722 A1 | 3/2007 | Salonen et al. |
| 2007/0196841 A1 | 8/2007 | Ruano et al. |
| 2007/0218519 A1 | 9/2007 | Urdea et al. |
| 2008/0227210 A1 | 9/2008 | Smith |
| 2008/0293054 A1 | 11/2008 | Medina et al. |
| 2008/0300170 A1 | 12/2008 | Gelber et al. |
| 2009/0197242 A1 | 8/2009 | Kaddurah-Daouk et al. |
| 2009/0246801 A1 | 10/2009 | Smith |
| 2010/0063153 A1 | 3/2010 | Chatterjee et al. |
| 2010/0076787 A1 | 3/2010 | Naylor et al. |
| 2010/0120136 A1 | 5/2010 | Larsen et al. |
| 2010/0167306 A1 | 7/2010 | Smith |
| 2010/0190172 A1 | 7/2010 | Cargill et al. |
| 2010/0204557 A1 | 8/2010 | Kiaie et al. |
| 2011/0112186 A1 | 5/2011 | Link et al. |
| 2011/0250618 A1 | 10/2011 | Nelson et al. |
| 2011/0269735 A1 | 11/2011 | Shiffman et al. |
| 2012/0065514 A1 | 3/2012 | Naghavi et al. |

FOREIGN PATENT DOCUMENTS

| | | |
|---|---|---|
| WO | 02/48715 | 6/2002 |
| WO | 2004/050898 A2 | 6/2004 |
| WO | WO-2005/012566 A2 | 2/2005 |
| WO | WO-2006/008656 A2 | 1/2006 |
| WO | WO-2006/072654 A1 | 7/2006 |
| WO | WO-2007/012884 A1 | 2/2007 |
| WO | WO-2007/061995 A2 | 5/2007 |
| WO | 2007/128884 A1 | 11/2007 |
| WO | 2008/131224 A2 | 10/2008 |
| WO | WO-2009/106838 A1 | 9/2009 |
| WO | WO-2011/058232 A1 | 5/2011 |
| WO | WO-2013/078122 A1 | 5/2013 |

OTHER PUBLICATIONS

Perk J, De Backer G, Gohlke H, et al. European Guidelines on cardiovascular disease prevention in clinical practice (version 2012): The Fifth Joint Task Force of the European Society of Cardiology and Other Societies on Cardiovascular Disease Prevention in Clinical Practice (constituted by representatives of nine societies and by invited experts) Developed with the special contribution of the European Association for Cardiovascular Prevention & Rehabilitation (EACPR). Eur Heart J 2012;33:1635-701.
Reihnér E, Rudling M, Ståhlberg D, et al. Influence of pravastatin, a specific inhibitor of HMG-CoA reductase, on hepatic metabolism of cholesterol. N Engl J Med 1990;323:224-8.
Lamon-Fava S, Diffenderfer MR, Barrett PH, et al. Effects of different doses of atorvastatin on human apolipoprotein B-100, B-48, and A-I metabolism. J Lipid Res 2007;48:1746-53.
Vanhanen H, Miettinen TA. Pravastatin and lovastatin similarly reduce serum cholesterol and its precursor levels in familial hypercholesterolaemia. Eur J Clin Pharmacol 1992;42:127-30.
Ooi EM, Barrett PH, Chan DC, Nestel PJ, Watts GF. Dose-dependent effect of rosuvastatin on apolipoprotein B-100 kinetics in the metabolic syndrome. Atherosclerosis 2008;197:139-46.
De Cuyper I, Wolthers BG, van Doormaal JJ, Wijnandts PN. Determination of changes in serum lathosterol during treatment with simvastatin to evaluate the role of lathosterol as a parameter for whole body cholesterol synthesis. Clin Chim Acta 1993;219:123-30.
Miettinen TA, Gylling H, Lindbohm N, Miettinen TE, Rajaratnam RA, Relas H. Serum noncholesterol sterols during inhibition of cholesterol synthesis by statins. J Lab Clin Med 2003;141:131-7.
van Himbergen TM, Matthan NR, Resteghini NA, et al. Comparison of the effects of maximal dose atorvastatin and rosuvastatin therapy on cholesterol synthesis and absorption markers. J Lipid Res 2009;50:730-9.

Davidson MH, McGarry T, Bettis R, et al. Ezetimibe coadministered with simvastatin in patients with primary hypercholesterolemia. J Am Coll Cardiol 2002;40:2125-34.
Gagne C, Gaudet D, Bruckert E. Efficacy and safety of ezetimibe coadministered with atorvastatin or simvastatin in patients with homozygous familial hypercholesterolemia. Circulation 2002;105:2469-75.
Sudhop T, Lutjohann D, Kodal A, et al. Inhibition of intestinal cholesterol absorption by ezetimibe in humans. Circulation 2002;106:1943-8.
Gouni-Berthold I, Berthold HK, Gylling H, et al. Effects of ezetimibe and/or simvastatin on LDL receptor protein expression and on LDL receptor and HMG-CoA reductase gene expression: a randomized trial in healthy men. Atherosclerosis 2008;198:198-207.
Ballantyne CM, Houri J, Notarbartolo A, et al. Effect of ezetimibe coadministered with atorvastatin in 628 patients with primary hypercholesterolemia: a prospective, randomized, double-blind trial. Circulation 2003;107:2409-15.
Morrone D, Weintraub WS, Toth PP, Hanson ME, Lowe RS, Lin J, Shah AK, and Tershakovec AM. Lipid-altering efficacy of ezetimibe plus statin and statin monotherapy and identification of factors associated with treatment response: A pooled analysis of over 21,000 subjects from 27 clinical trials. Atherosclerosis , in press. 2012.
Pearson TA, Denke MA, McBride PE, Battisti WP, Brady WE, Palmisano J. A community-based, randomized trial of ezetimibe added to statin therapy to attain NCEP ATP III goals for LDL cholesterol in hypercholesterolemic patients: the ezetimibe add-on to statin for effectiveness (EASE) trial. Mayo Clin Proc 2005;80:587-95.
Pearson TA, Denke MA, McBride PE, et al. Effectiveness of ezetimibe added to ongoing statin therapy in modifying lipid profiles and low-density lipoprotein cholesterol goal attainment in patients of different races and ethnicities: a substudy of the Ezetimibe add-on to statin for effectiveness trial. Mayo Clin Proc 2006;81:1177-85.
Friedewald WT, Levy RI, Fredrickson DS. Estimation of the concentration of low-density lipoprotein cholesterol in plasma, without use of the preparative ultracentrifuge. Clin Chem 1972;18:499-502.
Miettinen TA, Tilvis RS, Kesaniemi YA. Serum plant sterols and cholesterol precursors reflect cholesterol absorption and synthesis in volunteers of a randomly selected male population. Am J Epidemiol 1990;131:20-31.
Assmann G, Kannenberg F, Ramey DR, Musliner TA, Gutkin SW, Veltri EP. Effects of ezetimibe, simvastatin, atorvastatin, and ezetimibe-statin therapies on non-cholesterol sterols in patients with primary hypercholesterolemia. Curr Med Res Opin 2008;24:249-59.
Davidson MH, Ballantyne CM, Kerzner B, et al. Efficacy and safety of ezetimibe coadministered with statins: randomised, placebo-controlled, blinded experience in 2382 patients with primary hypercholesterolemia. Int J Clin Pract 2004;58:746-55.
Miettinen TA, Strandberg TE, Gylling H. Noncholesterol sterols and cholesterol lowering by long-term simvastatin treatment in coronary patients: relation to basal serum cholestanol. Arterioscler Thromb Vasc Biol 2000;20:1340-6.
Nissinen MJ, Miettinen TE, Gylling H, Miettinen TA. Applicability of non-cholesterol sterols in predicting response in cholesterol metabolism to simvastatin and fluvastatin treatment among hypercholesterolemic men. Nutr Metab Cardiovasc Dis 2010;20:308-16.
Jakulj L, Vissers MN, Groen AK, et al. Baseline cholesterol absorption and the response to ezetimibe/simvastatin therapy: a post-hoc analysis of the ENHANCE trial. J Lipid Res 2010;51:755-62.
Lakoski SG, Xu F, Vega GL, et al. Indices of Cholesterol Metabolism and Relative Responsiveness to Ezetimibe and Simvastatin. J Clin Endocrinol Metab 2010;95:800-9.
Ahern et al., Biochemical, Reagent Kits Offer Scientists Good Return on Investment, The Science, vol. 9, pp. 1-5, 1995.
Armitage, J., "The safety of statins in clinical practice," Lancet, 2007, pp. 1781-1790, vol. 370.

(56) References Cited

OTHER PUBLICATIONS

Asztalos B F et al: "LpA-I, LpA-I:A-II HDL and CHD-risk: The Framingham Offspring Study and the Veterans Affairs HDL Intervention Trial", Atherosclerosis, vol. 188, No. 1, Sep. 1, 2006 (Sep. 1, 2006), pp. 59-67, XP028071474, Elsevier Ireland Ltd, Dublin ISSN: 0021-9150, DOI: 10.1016/J.Atherosclerosis.2005.10.018.
Asztalos, B.F., et al., "Distribution of ApoA-I-containing HDL Subpopulations in Patients with Coronary Heart Disease," Arterioscler Thromb Vasc Biol., Dec. 2000; 20(12)2670-6.
Asztalos, B.F., et al., "High-density Lipoprotein Subpopulation Profile and Coronary Heart Disease Prevalence in Male Participants of the Framingham Offspring Study," Arterioscler Thromb Vasc Biol., Nov. 2004; 24(11):2181-7.
Asztalos, B.F., et al., "Two-dimensional electrophoresis of plasma lipoproteins: recognition of new apo A-I-containing subpopulations," Biochim Biophys Acta., Sep. 8, 1993; 1169(3):291-300.
Asztalos, B.F., et al., "Value of High-Density Lipoprotein (HDL) Subpopulations in Predicting Recurrent Cardiovascular Events in the Veterans Affairs HDL Intervention Trial," Arterioscler Thromb Vasc Biol., Oct. 2005; 25(10):2185-2191.
Ballantyne, C.M., et al., "Risk for myopathy with statin therapy in high-risk patients," Arch Intern Med, 2003, pp. 553-564, vol. 163.
Barrett, J.C., et al., Haploview: analysis and visualization of LD and haplotype maps, Bioinformatics, 2005, pp. 263-265, vol. 21.
Bland et al., "Multiple significance tests: the Bonferroni method," BMJ, vol. 310, p. 170, Jan. 21, 1995.
Burke et al.,Mechanisms of the Liebermann-Burchard and Zak Color Reactions for Cholesterol, Clin. Chem .20(7), 794-801, 1974.
Burke, J. P., et al., "Rapid Rise in the Incidence of Type 2 Diabetes From 1987 to 1996," (1999) Arch Intern Med. 159:1450-1456.
Camont et al: "Biological activities of HDL subpopulations and their relevance to cardiovascular disease", Trends in Molecular Medicine, vol. 17, No. 10, Oct. 1, 2011.
Carlton et al., "Functional single nucleotide polymorphism-based association studies," Human Genomics, 2(6): 391-402 (2006).
Cholesterol Treatment Trialists' (CTT) Collaborators, Efficacy and safety of cholesterol-lowering treatment: prospective meta-analysis of data from 90,056 participants in 14randomised trials of statins, Lancet, 2005, pp. 1267-1278, vol. 366.
Corsini, A., et al., "Pharmacokinetic interactions between statins and fibrates," Am J. Cardiol, 2005,pp. 44K-49K, vol. 96.
Couvert P et al, Association between a Frequent Allele of the Gene Encoding OATP1B1 and the Enhanced LDL-Lowering Response to Fluvastatin Therapy, Pharmacogenomics 9: 1217-1227, 2008.
Cuyper et al., Determination of changes in serum lathosterol during treatment with simvastatin to evaluate the role of lathosterol as a parameter for whole body cholesterol synthesis. Clin Chim Acta 1993;219:123-30.
Davis, H et al. Zetia: Inhibition of Niemann-Pick C1 Like 1 (NPC1L1) to Reduce Intestinal Cholesterol Absorption and Treat Hyperlipidemia. Journal of Atherosclerosis and Thrombosis. May 2007, vol. 14; pp. 99-108.
Deepak Voora et al., The SLCO1B18*5 Genetic Variant is Associated with Statin-Induced Side Effects, Journal of the American College of Cardiology, vol. 54, No. 17, 2009, pp. 1609-1616.
Devlin, B., et al., "Genomic control for association studies," Biometrics, 1999, pp. 997-1004, vol. 55.
Dullaart RPF et al, The Serum Lathosterol to Cholesterol Ratio, an Index of Cholesterol Synthesis,is Not Elevated in Patients With Glomerular Proteinuria and is Not Associated With Improvement of Hyperlipidemia in Response to Antiproteinuric Treatment, Metabolism 45: 723-730, 1996.
Espy et al (2006) Clin Microbiol Rev. Jan. 2006; 19(1): 165-256.
Farnier, M et al. Lipid-Altering Eficacy of Ezetimibe/Simvastatin 10/20 mg Compared With Rosuvastatin 10 mg in High-Risk Hypercholesterolaemic Patients Inadequately Controlled With Prior Statin Monotherapy—The In-Cross Study. The International Journal of Clinical Practice. Apr. 2009, vol. 63; pp. 547-559.

Fiegenbaum et al., "The role of common variants of ABCB1, CYP3A4, and CYP3A5 genes in lipidlowering efficacy and safety of simvastatin treatment," Clin. Pharmocol. Ther., vol. 78, pp. 551-558, 2005.
Frudakis et al., "CYP2D6*4 polymorphism is associated with statin-induced muscle effects," Pharmacogenetics and Genomics, vol. 17, pp. 695-707, 2007.
Gazi IF et al, Effect of Ezetimibe in Patients Who cannot Tolerate Statins or cannot Get to the Low Density Lipoprotein Cholesterol Target Despite Taking a Statin, Crur Med Res Opin 23: 2183-2192, 2007.
Generaux GT et al, Impact of SLCO1B1 (OATP1B1) and ABCG2 (BCRP) Genetic Polymorphisms and Inhibition on LDL-C Lowering and Myopathy of Statins, Xenobiot 41: 639-651, 2011.
Goh et al., HPLC analysis of desmosterol, 7-dehydrocholesterol, and cholesterol. Lipids 24.7 (1989): 652-655.
Gordon, D.J. et al., "High-density Lipoprotein Cholesterol and Cardiovascular Disease. Four Prospective American Studies," Circulation, Jan. 1989; 79(1):8-15.
Grundy et al., "Plasma Non-Cholesterol Sterols as Indicators of Cholesterol Absorption." Journal of lipid research (2013) V54 873-875.
Gunderson, K.L., et al., "Whole-genome genotyping of haplotype tag single nucleotide polymorphisms," Pharmacogenomics, 2006, pp. 641-648, vol. 7.
Havekes LM et al. A rapid micro method for apolipoprotein E phenotyping directly in serum. J Lipid Res (1987) 28:455-63.
Heart Protection Study Collaborative Group, "MRC/BHF Heart Protection Study of cholesterol lowering with simvastatin in 20,536 high-risk individuals: a randomised placebo-controlled trial," Lancet, 2002, pp. 7-22, vol. 360.
Hermann et al., "Pharmacokinetics and Drug Disposition: Exposure of atorvastatin is unchangedbut lactone and acid metabolites are increased several-fold in patients with atorvastatin-induced myopathy," Clinical Pharmacology & Therapeutics, vol. 79, No. 6, pp. 532-539, 2006.
Himbergen et al., Comparison of the effects of maximal dose atorvastatin and rosuvastatin therapy on cholesterol synthesis and absorption markers. J Lipid Res 2009;50:730-9.
Hironobu Akao et al., Genetic Variation at the SLCO1B1 Gene Locus and Low Density Lipoprotein Cholesterol Lowering Response to Pravastatin in the Elderly, Atherosclerosis, 220, 2012, pp. 413-417.
Ho et al., "Drug and Bile Acid Transporters in Rosuvastatin Hepatic Uptake: Function, Expression, and Pharmacogenetics," Gastroenterology, 130(6): 1793-1806 (2006).
Hsiang et al., "A Novel Human Hepatic Organic Anion Transporting Polypeptide (OATP2): Identification of a liver-specific human organic anion transporting polypeptide and identification of rat and human hydroxymethylglutaryl-CoA reductase inhibitor transporters," J. Biol. Chem., 274(52): 37161-37168 (1999).
International Hapmap Consortium, "A haplotype map of the human genome," Nature, 2005, pp. 1299-1320, vol. 437.
International Search Report for PCT/GB2009/000547, dated May 11, 2009, 4 pages.
International Search Report and Written Opinion for PCT/US12/60014, dated Apr. 5, 2013, 9 pages.
International Search Report and Written Opinion for PCT/US2013/066860 dated Jan. 20, 2014, 14 pages.
International Search Report and Written Opinion for PCT/US2013/62241 dated Jan. 17, 2014, 16 pages.
Isbell et al: "Reproducibility and Reliability of Atherosclerotic Plaque Volume Measurements in Peripheral Arterial Disease with Cardiovascular Magnetic Resonance", Journal of Cardiovascular Magnetic Resonance, vol. 9, No. 1, Jan. 1, 2007, p. 1-15.
Juraschek et al., Alternative Markers of Hyperglycemia and Risk of Diabetes, vol. 35 No. 11, Aug. 8, 2012, p. 1-6.
Kajinami, K., et al., "CYP3A4 genotypes and plasma lipoprotein levels before and after treatment with atorvastatin in primary hypercholesterolemia," Am J Cardiol, 2004, pp. 104-107, vol. 93.
Kameyama et al., "Functional characterization of SLCO1B1 (OATP-C) variants, SLCO1B1*5,SLCO1B1*15 and SCL01B1*15+C1007G, by using transient expression systems of

(56) References Cited

OTHER PUBLICATIONS

HeLa and HEK293 cells," Pharmacogenetics and Genomics, vol. 15, No. 7, pp. 513-522. Jul. 2005.

Kim et. al., "3-Hydroxy-3-methylglutaryl-coenzyme A reductase inhibitors (statins) and genetic variability(single nucleotide polymorphisms) in a hepatic drug uptake transporter: What's it all about?," Clinical Pharmacology & Therapeutics, vol. 75, No. 5, pp. 381-385, 2004.

Kim, K.T., et al., "Increased systemic exposure to rosuvastatin in Asian subjects residing in the United States compared to Caucasian subjects," Clinical Pharmacology and Therapeutics, 2008, p. S 14,vol. 83.

Kivisto et al., "Influence of Drug Transporter Polymorphisms on Pravastatin Pharmacokinetics in Humans," Pharmceutical Research, vol. 24, No. 2, pp. 239-247, Feb. 2007.

Kolberg, J. A., et al., "Development of a Type 2 Diabetes Risk Model From a Panel of Serum Biomarkers From the Inter99 Cohort," (2009) Diabetes Care 32(7):1207-12.

Konig, J., et al., Pharmacogenomics of human OATP transporters, Naunyn Schmiedebergs Arch Pharmacol2006, pp. 432-443, vol. 372.

Law, M., et al., "Statin safety: a systematic review," Am J. Cardiol, 2006, pp. S52-S60, vol. 97.

Link et al., "SLCO1B1 Variants and Statin-Induced Myopathy—A Genomewide Study," N. Engl. J. Med., 359: 789-799 (2008).

Lund, E., et al. "Determination of serum levels of unesterified lathosterol by isotope dilution-mass spectrometry." Scandinavian journal of clinical & laboratory investigation 49.2 (1989): 165-171.

Luzón-Toro et al., "Gas chromatographic-mass spectrometric determination of brain levels of α-cholest-8-en-3β-ol (lathosterol)." Journal of Chromatography B 850.1 (2007): 177-182.

Mangravite, L.M., et al., "Clinical implications of pharmacogenomics of statin treatment," Pharmacogenomics J, 2006, pp. 360-374, vol. 6.

Mann, D. M., et al., "The Multi-Ethnic Study of Atherosclerosis," (MESA) (2010) Am J Epidemiol 171(9):980-988. Jan. 2010.

Matthan NR et al., Impact of simvastatin, niacin, and/or antioxidants on cholesterol metabolism in CAD patients with low HDL. J Lipid Res. 2003;44:800-806.

Matthan NR et al., "Deuterium uptake and plasma cholesterol precursor levels correspond as methods for measurement of endogenous cholesterol synthesis in hypercholesterolemic women.", Lipids. 2000;35:1037-1044.

Matthan, N et al. Cholesterol Absorption and Synthesis Markers in Individuals With and Without a CHD Event During Pravastatin Therapy: Insights From The PROSPER Trial. Journal of Lipid Research. Jul. 3, 2009, vol. 51; pp. 202-209.

Mikko Niemi et al., Organic Anion Transporting Polypeptide 1B1: a Genetically PolymorphicTransporter of Major Impotence for Hepatic Drug Uptake, Pharmacological Reviews, vol. 63, No. 1, 2011, pp. 157-181.

Molden, E., "Variability in Cytochrome P450-Mediated Metabolism of Cardiovascular Drugs: Clinical Implications and Practical Attempts to Avoid Potential Problems," Heart Drug, 2004, pp. 55-79, vol. 4.

Morimoto et al., "Candidate gene approach for the study of genetic factors involved in HMG-CoA reductase inhibitor-induced rhabdomyolysis," Eighteenth JSSX Annual Meeting, 8PE-32 (2003).

Morimoto et al; A Novel Variant Allele of OATP-C (SLCO1B1) Found in a Japan Patient with Pravastatin-induced Myopathy, Drug Metab. Pharmocokinet. vol. 19, pp. 453-455; 2004.

Morimoto, K, et al., "OATP-C(OATP01B1)*15 is associated with statin-induced myopathy in hypercholesterolemia patients," Clinical Pharmacology & Therapeutics, 2005, pp. P21-P21 vol. 77.

Mulder et al., "Association of polymorphism in the cytochrome CYP2D6 and the efficacy and tolerability of simvastatin," Clin. Pharmacol. Ther., vol. 70, pp. 546-551, 2001.

Márk, L et al., Change in the cholesterol metabolism associated with the combined inhibition of synthesis and absorption. Orvosi hetilap 148.14 (2007): 627.

Nauck et al., Clinical Chemistry Feb. 2002 vol. 48 No. 2 236-254.

Niemi et al., "Acute effects of pravastatin on cholesterol synthesis are associated with SLCO1B1(encoding OATP1B1) haplotype *17," Pharmacogenet. Genomics, vol. 15, No. 5, pp. 303-309, May 15, 2005.

Niemi et al., "High plasma pravastatin concentrations are associated with single nucleotide polymorphisms and haplotypes of organic anion transporting polypeptide-C (OATP-C, SCL01B1)," Pharmacogenetics, 14: 429-440 (2004).

Nishizato et al., "Polymorphisms of OATP-C (SLC21A6) and OAT3 (SLC22A8) genes: Consequences for pravastatin pharmacokinetics," Clin. Pharmacol. Ther., 73(6): 554-565 (2003).

Nozawa et al.,"Genetic Polymorphisms of Human Organic Anion Transporters OATP-C(SLC21A6) and OATP-B (SLC21A9): Allele Frequiences in the Japanese Population and Functional Analysis," The Journal of Pharmacology and Experimental Therapeutics, vol. 302, No. 2, pp. 2002.

Oh, J., et al., "Genetic determinants of statin intolerance," Lipids Health Dis, 2007, pp. 6:7.

Ordovas JM et al, The APOE Locus and the Pharmacogenetics of Lipid Response, Cur Opin Lipidol 13: 113-117, 2002.

Pasanen et al., "Different Effects of SLCO1B1 Polymorphism on the Pharmacokinetics of Atorvastatin and Rosuvastatin," Clin. Pharmacol. Ther., 82(6): 726-733 (2007).

Pasanen et al., "Global analysis of genetic variation in SLCO1B1," Pharmacogenomics, vol. 9, No. 1, pp. 19-33, Jan. 2008.

Pasanen et al.,"SLCO1B1 polymorphism markedly affects the pharmacokinetics of simvastatinacid," Pharmacogenet. Genomics, vol. 16, No. 12, pp. 873-879, Dec. 2006.

Pasanen et al.; Frequencies of single nucleotide polymorphisms and haplotypes of organic anion transporting polypeptide 1B1 SLCO1B1 gene in a Finnish population, Eur. J, Clin. pharmacol. vol. 62, pp. 409-415; 2006.

Price, A.L., et al., "Principal components analysis corrects for stratification in genome-wide association studies," Nat Genet, 2006, pp. 904-909, vol. 38.

Purcell, S., et al., "PLINK: a tool set for whole-genome association and population-based linkage analyses," Am J Hum Genet, 2007, pp. 559-575, vol. 81.

R Development Core Team, "R: A Language and Environment for Statistical Computing," Vienna, Austria: R Foundation for Statistical Computing, 2007.

Robinson, "Simvastatin: present and future perspectives," Expert Opin. Pharmacother., 8(13): 2159-2172 (2007).

Romaine SPR et al, The Influence of SLCO1B1 (OATP1B1) Gene Polymorphisms on Response to Statin Therapy,Pharmacogenom J 10: 1-11, 2010.

Ruano et al., Physiogenomic Association of Statin-Related Myalgia to Serotonin Receptors, Muscle Nerve, vol. 36, pp. 329-335, 2007.

Schaffer, R., et al. "Comparison of two isotope dilution/mass spectrometric methods for determination of total serum cholesterol." Clinical chemistry 28.1 (1982): 5-8.

Schmidt, M. I., et al., "The Atherosclerosis Risk in Communities study," (2005) Diabetes Care 28(8):2013-2018.

Search Study Collaborative Group, "Study of the effectiveness of additional reductions in cholesterol and homocysteine (SEARCH): characteristics of a randomized trial among 12064 myocardial infarction survivors," Am Heart J, 2007, pp. 815-823, vol. 154, No. e6.

Shitara et al., "Pharmacokinetic and pharmacodynamic alterations of 3-hydroxy- 3-methylglutaryl coenzyme A (HMG-CoA) reductase inhibitors: drug-drug interactions and interindividual differences in transporter and metabolic enzyme functions," Pharmacol Ther, 2006, pp. 71-105, vol. 112.

Simonson, S.G., et al., "Rosuvastatin pharmacokinetics in heart transplant recipients administered an antirejection regimen including cyclosporine," Clin Pharmacol Ther, 2004, pp. 167-177, vol. 76.

Stern, M. P., et al., Predicting Diabetes, "Moving Beyond Impaired Glucose Tolerance," (1993) Diabetes 42:706-714.

(56) References Cited

OTHER PUBLICATIONS

Stern, M. P., et al., The San Antonio Heart Study, "Sex Difference in the Effects of Sociocultural Status on Diabetes and Cardiovascular Risk Factors in Mexican Americans," (1984) Am. J. Epidemiol. 120(6):834-851.
Streiner et al., "Correction for Multiple Testing, Is there a resolution?," Chest, vol. 140, No. 1, pp. 16-18, Jul. 2011.
Sugiuchi et al., Clinical Chemistry 44:3 522-531 (1998).
The Search Collaborative Group, The New England Journal of Medicine, SLC01B1 Variants and Statin-Induced Myopathy—A Genomewide Study, vol. 359, No. 8, Aug. 21, 2008, pp. 789-799.
Thompson, P.D., et al., "Statin-associated myopathy," JAMA, 2003, pp. 1681-1690, vol. 289.
Thongtang et al., "Effects of ezetimibe added to statin therapy on markers of cholesterol absorption and synthesis and LDL-C lowering in hyperlipidemic patients," Atherosclerosis, vol. 225, Issue 2, Dec. 2012, pp. 388-396.
Tirona, R.G., et al., "Polymorphisms in OATP-C: identification of multiple allelic variants associated with altered transport activity among European- and African-Americans," J Biol Chem, 2001, pp. 35669-35675, vol. 276.
Tobert, "Lovastatin and Beyond: The History of the HMG-CoA Reductase Inhibitors," Nat. Rev. Drug Discov., 2(7): 517-526 (2003).
Tyburczy et al., "Evaluation of low trans-fat edible oils by attenuated total reflection-Fourier transform infrared spectroscopy and gas chromatography: a comparison of analytical approaches." Analytical and bioanalytical chemistry 404.3 (2012): 809-819.
United Kingdom Search Report issued in application No. GB0803833.3 on Jun. 27, 2008.
Uusitupa MIJ et al, Lathosterol and Other Noncholesterol Sterols During Treatment of Hypercholesterolemia With Lovastatin Alone and With Cholestyramine or Guar Gum, Arterioscler Thromb 12: 807-813, 1992.
Vladutiu, et al., "Genetic risk factors associated with lipid-lowering drug-induced myopathies, Muscle Nerve," 2006, pp. 153-162, vol. 34.
Warnick et al., Clinical Chemistry Sep. 2001 vol. 47 No. 9 1579-1596.
Wellcome Trust Case Control Consortium, "Genome-wide association study of 14,000 cases of seven common diseases and 3,000 shared controls," Nature, 2007, pp. 661-678, vol. 447.
Wilson, P. W. F., et al., The Framingham Offspring Study, "Prediction of Incident Diabetes Mellitus in Middle-aged Adults," (2007) Arch Intern Med. 167(10):1068-1074.
Xu et al., "Organic anion transporting polypeptide-1B1 haplotypes in Chinese patients," Acta Pharmacologica Sinica, vol. 28, No. 10, pp. 1693-1697, Oct. 28, 2007.
Zocor datasheet, 2007.httD://www.emc.medicines.ora.uk/emc/assets/c/htmllDisDlavDoc.asD?DocumentID=120.
Zuccaro et al.t "Tolerability of statins is not linked to CYP450 polymorphisms, but reduced CYP2D6 metabolism improves cholesteraemic response to simvastatin and fluvastatin," Pharmacological Research, vol. 55, pp. 310-317, 2007.
Anderson, 2010, The Clinical Plasma Proteome: A Survey of Clinical Assays for Proteins in Plasma and Serum, Clinical Chemistry 56(2):177-185.
Brambilla et al., 2011, Normal Fasting Plasma Glucose and Risk of Type 2 Diabetes, Diabetes Care 34:1372-1374.
Cruz et al., 2004, Low Adiponectin Levels Predict Type 2 Diabetes in Mexican Children, Diabetes Care 27(6):1451-1453.
Degn et al., 2004, One Week's Treatment With the Long-Acting Glucagon-Like Peptide 1 Derivative Liraglutide (NN2211) Markedly Improves 24-h Glycemia and-and-Cell Function and Reduces Endogenous Glucose Release in Patients with Type 2 Diabetes, Diabetes 53:1187-1194.
Eddy et al., 2003, A trial-validated model of diabetes, Diabetes Care 26(11):3093-3101.
Eddy et al., 2003, Validation of the Archimedes Diabetes Model, Diabetes Care 26(11):3102-3110.
Fumeron et al., 2004, Adiponectin Gene Polymorphisms and Adiponectin Levels Are Independently Associated With the Development of Hyperglycemia During a 3-Year Period; The Epidemiologic Data on the Insulin Resistance Syndrome Prospective Study, Diabetes 53:1150-1157.
Harder et al., 2004, The Effect of Liraglutide, a Long-Acting Glucagon-Like Peptide 1 Derivative, on Glycemic Control, Body Composition, and 24-h Energy Expenditure in Patients; With Type 2 Diabetes, Diabetes Care 27(8):1915-1921.
Kaput et al., 2004, Nutritional genomics: the next frontier in the postgenomic era, Physiol Genomics 16:166-177.
Kaput et al., 2007, Application of nutrigenomic concepts to Type 2 diabetes mellitus, Nutrition, Metabolism & Cardiovascular Diseases 17:89-103.
Kaput, 2004, Diet-Disease Gene Interactions, Nutrition 20:26-31.
Krakoff et al., 2003, Inflammatory Markers, Adiponectin, and Risk of Type 2 Diabetes in the Pima Indian, Diabetes Care 26(6):1745-1751.
Lindstrom et al., 2003, The Diabetes Risk Score, Diabetes Care 26(3):725-731.
Lyssenko et al., 2005, Genetic Prediction of Future Type 2 Diabetes, PLoS Medicine 2(12):e345.
Madsbad et al., 2004, Improved Glycemic Control With No Weight Increase in Patients With Type 2 Diabetes After Once-Daily Treatment With the Long-Acting Glucagon-Like Peptide 1 Analog Liraglutide (NN2211), Diabetes Care 27(6):1335-1342.
Patent Examination Report No. 1 date of issue Jun. 11, 2014 for Patent Application No. AU 2011/261480.
Pradhan et al., 2001, C-Reactive Protein, Interleukin 6, and Risk of Developing Type 2 Diabetes Mellitus, JAMA 286(3):327-334.
Programme for the Prevention of Type 2 Diabetes in Finland, Finnish Diabetes Association, 2003-2010, Published in 2003.
Ravussin, 2002, Adiponectin enhances insulin action by decreasing ectopic fat deposition, The Pharmacogenomics Journal 2:4-7.
Schaefer et al., Association of Statin Potency with Markers of Cholesterol Absorption/Synthesis and LDL-C Lowering Efficacy of Ezetimibe Add on Therapy, J of Clinical Lipidology 6(3)286 abstract 160, Jun. 2012.
Spranger et al., 2003, Adiponectin and protection against type 2 diabetes mellitus, Lancet 361:226-228.
Sturis et al., 2003, GLP-1 derivative liraglutide in rats with b-cell deficiencies: influence of metabolic state on b-cell mass dynamics, British Journal of Pharmacology 140:123-132.

\* cited by examiner

DRIVING PATIENT COMPLIANCE WITH THERAPY

TECHNICAL FIELD

The invention generally relates to methods for determining whether a patient is complying with cholesterol reducing therapy and corresponding therapeutic methods.

BACKGROUND

Cholesterol is an essential structural component of mammalian cell membranes and is required to establish proper membrane permeability and fluidity. In addition to its importance within cells, cholesterol also serves as a precursor for the biosynthesis of steroid hormones, bile acids, and vitamin D.

Although cholesterol is important and necessary for human health, high levels of cholesterol in the blood have been linked to damage to arteries and cardiovascular disease. For high risk patients, their cholesterol level is routinely monitored. Standard cholesterol screening tests are conducted by obtaining a blood sample from a patient and measuring a total cholesterol level, a low density lipoprotein cholesterol (LDL-C or LDL cholesterol) level, and a high density lipoprotein cholesterol (HDL-C or HDL cholesterol) level. The LDL cholesterol is also known as "bad cholesterol" because it promotes plaque formation on the inner walls of arteries. Together with other substances, LDL-C cholesterol is thought to cause atherosclerosis. If a clot forms and blocks a narrowed artery, a heart attack or stroke can result.

There are two mechanisms that result in LDL-C in the body: production of cholesterol from the liver and absorption of cholesterol from the diet. Each mechanism can be controlled by a different LDL-C lowering drug. A common practice of health care providers is to prescribe a statin therapy to a patient with high LDL-C and to monitor the patient's response to statin therapy in order to guide future therapeutic decisions.

SUMMARY

The invention recognizes that while cholesterol lowering therapies, such as statins, are effective in lowering LDL-C and increasing HDL-C, patients often do not adhere to or discontinue their statin therapy because of certain undesirable side effects (e.g., muscle pain and digestive problems), and do not disclose such noncompliance to their health care provider. Without that information, the health care provider is unable to determine the root cause of the patient's response to statin therapy. As a result, health care providers often prescribe an improper therapeutic regime that may increase the time it will take the patient to reach his or her LDL-C lowering goals.

The present invention provides objective assay-based methods for monitoring a patient's compliance with his/her cholesterol lowering therapy. Accordingly, methods of the invention do not rely on patient self-reporting to determine whether a patient has complied with their cholesterol lowering therapy. Aspects of the invention are accomplished by conducting assays to analyze a cholesterol level and to analyze biomarkers that are indicative of a patient's ability to absorb and/or produce LDL-cholesterol. That analysis allows a health care provider to objectively determine a patient's non-compliance with statin therapy. By identifying non-compliance using methods of the invention, a healthcare provide is able to identify the root cause of a patient's LDL-C levels during therapy and objectively determine the appropriate drugs to administer the patient in order to assist the patient in efficiently reaching his LDL-C goals.

For example, a patient who is prescribed a statin but is non-compliant will not see lower LDL-C levels at subsequent visits. This may be because a non-compliant patient who is an over-producer of cholesterol will exhibit comparable LDL-C levels as to a patient who is a hyper-absorber of cholesterol on the same statin therapy. Without knowing the patient's compliance, a provider's typical response is to prescribe an increased dosage of the statin or prescribe a different drug such as an absorption inhibiting drug. If a non-compliant, over-producer patient is placed on such cholesterol absorption inhibitor therapy, the patient may not beneficially respond to such therapy and his/her LDL-C levels may plateau or increase, thereby increasing the time it takes to reach his/her LDL-C goals. The same is true when a non-compliant, over-absorber patient is placed on a higher dosage of a statin. Instead of using trial and error to determine the appropriate LDL-C lowering therapy, methods of the invention are able to identify the non-compliant patient and guide a physician towards a treatment plan that makes the most efficient use of the LDL-C lowering drugs.

In certain aspects, methods of the invention involve conducting an assay to determine a cholesterol biomarker level in a sample of the patient. Based on the cholesterol biomarker level, a course of treatment to lower cholesterol for the patient is provided. An assay is then conducted to determine a level of cholesterol of the patient undergoing the course of treatment. Based on the cholesterol level and the cholesterol biomarker level, the patient's compliance with the course of treatment is determined. In certain embodiments, the cholesterol biomarker is a cholesterol absorption biomarker, a cholesterol production biomarker, or combination of both. The cholesterol lowering therapy may include a drug that inhibits cholesterol production (e.g. a statin), a drug that inhibits cholesterol absorption (e.g. ezetimibe), or a combination of both. It is understood that levels of total cholesterol, HDL cholesterol and LDL cholesterol may be monitored and assayed to assess compliance using methods of the invention.

Methods of the invention include prescribing a course of treatment for reducing cholesterol based on a level of a cholesterol biomarker and a first (i.e. reference level) of cholesterol, such as LDL cholesterol, obtained from a sample from a patient. After which, an assay is conducted to determine a second level of LDL cholesterol in another sample from the patient while undergoing the course of treatment. The patient's compliance with the course of treatment is then determined based on the level of the cholesterol marker, the first level of cholesterol and the second level of cholesterol.

According to some embodiments, the patient's compliance with a cholesterol lowering therapy is determined by comparing a level of cholesterol obtained from a patient's sample during treatment to a reference level of cholesterol in order to detect a change in the patient's cholesterol in response to treatment. The reference level of LDL cholesterol may be, for example, the patient's level of cholesterol prior to initiation of cholesterol lowering therapy or the patient's level of cholesterol prior to a new or different cholesterol lowering therapy (e.g. higher dose or different drug). The detected change in cholesterol may then be assessed in view of the patient's cholesterol biomarker level (e.g. cholesterol absorption biomarker, cholesterol production biomarker or both) in order to determine the patient's compliance with cholesterol lowering therapy. The detected change in cholesterol may be about zero, an increase in cholesterol, or a decrease in cholesterol.

In certain embodiments, the detected change in cholesterol is assessed in light of a detected change in the patient's cholesterol biomarker level. For example, a level of a cholesterol biomarker is compared to a reference level of a cholesterol biomarker. The reference level of a cholesterol biomarker may be, for example, the patient's level of a cholesterol biomarker prior to initiation of statin therapy or the patient's level of a cholesterol biomarker prior to a new or different statin therapy regimen. The detected change in the cholesterol biomarker level may be about zero, an increase in the cholesterol biomarker level, or a decrease in cholesterol biomarker level.

According to certain embodiments, the patient compliance is determined based on a detected change between a level of cholesterol and a reference level of cholesterol. For example, a patient is classified as compliant, based on a decrease in cholesterol, when the course of treatment is statin therapy and the level of the cholesterol biomarker is indicative of normal cholesterol absorption. In another example, a patient is classified as noncompliant, based on a detected change of about zero or an increase in cholesterol, when the course of treatment is statin therapy and the level of the cholesterol biomarker is indicative of normal cholesterol absorption. For another example, a patient is classified as noncompliant, based on an increase in cholesterol, when the course of treatment is ezetimibe therapy and the level of the cholesterol biomarker is indicative of over cholesterol absorption. In yet another example, a patient is classified as compliant, based on a detected change of about zero or an increase in cholesterol, when the course of treatment is ezetimibe therapy and the level of the cholesterol biomarker is indicative of over cholesterol absorption.

Generally, methods of the invention are conducted using a blood sample, however, any tissue or body fluid sample that includes markers for cholesterol absorption or production may be used with methods of the invention e.g., fecal or urine samples. Methods of the invention further involve conducting an assay on the sample to obtain a level of a cholesterol absorption marker and/or cholesterol production marker. Any cholesterol absorption marker or combination of cholesterol absorption markers may be used with methods of the invention. In certain embodiments, the cholesterol absorption marker is a steroid alcohol (sterol), such as campesterol or β-sitosterol. Any cholesterol production marker or combination of cholesterol production markers may be used with methods of the invention. For example, the cholesterol production markers are also sterols, such as lathosterol or desmosterol.

Methods of the invention are useful with any patients that are at risk of artery damage or developing a cardiovascular disease. Patient may have a high total cholesterol level, a high LDL level, or a combination thereof. The patient may or may not be already taking a cholesterol lowering drug. As discussed, the cholesterol lowering therapy may include a drug that inhibits cholesterol production (e.g. a statin), a drug that inhibits cholesterol absorption (e.g. ezetimibe), or a combination of both. The statin may be a low-potency statin, a medium potency statin, or a high-potency statin. In certain embodiments, the statin is a high-potency statin, such as simvastatin or atorvastatin.

Other aspects of the invention provide methods for determining whether a patient, either identified as compliant or non-compliant, should additionally be administered a different cholesterol lowering therapy. The different cholesterol lowering therapy may include, for example, different statin, a different dosage of statin, a drug that inhibits cholesterol absorption, or a combination thereof. Those methods involve conducting an assay to identify a level of a cholesterol absorption biomarker or a level of a cholesterol production biomarker, comparing the level of cholesterol to the level of the cholesterol absorption biomarker or the level of the cholesterol production biomarker, and determining the patient's compliance with statin therapy based said levels. Based on the patient's compliance, the patient is then administered a statin, a different dosage of statin, a drug that inhibits cholesterol absorption, or a combination thereof.

Other aspects of the invention provide methods that involve conducting a first assay to determine a cholesterol biomarker level in a first sample from a patient prior to the patient undergoing a cholesterol lowering therapy; conducting a second assay to determine a cholesterol level in a second sample obtained from the patient after the patient has started undergoing a cholesterol lowering therapy; and associating the cholesterol level and the cholesterol biomarker level, wherein the association allows for the determination of the patient's compliance with the cholesterol lowering therapy.

DETAILED DESCRIPTION

Methods of the invention can be used to determine a patient's compliance to a cholesterol lowering therapy in order to more effectively guide a physician towards a treatment plant that makes the most effective use of cholesterol (such LDL-cholesterol) lowering drugs. In certain embodiments, methods for determining a patient's compliance with a cholesterol lowering therapy involve conducting an assay to determine a cholesterol biomarker level in a sample of a patient, providing a course of treatment for the patient based on the cholesterol biomarker level, conducting an assay to determine a level of cholesterol of the patient undergoing the course of treatment, and determining the patient's compliance with the course of treatment based on the cholesterol level and the cholesterol biomarker level.

Other aspects of the invention provide methods that involve conducting a first assay to determine a cholesterol biomarker level in a first sample from a patient prior to the patient undergoing a cholesterol lowering therapy; conducting a second assay to determine a cholesterol level in a second sample obtained from the patient after the patient has started undergoing a cholesterol lowering therapy; and associating the cholesterol level and the cholesterol biomarker level, wherein the association allows for the determination of the patient's compliance with the cholesterol lowering therapy.

Methods of the invention are used to assess compliance of treatment for heart disease, such as statin therapy. Heart disease includes but is not limited to coronary heart disease (CHD), cardiomyopathy, cardiovascular disease (CVD), ischemic heart disease, heart failure, hypertensive heart disease, inflammatory heart disease, and valvular heart disease. Heart disease is a systemic disease that can affect the heart, brain, most major organs, and the extremities. Coronary heart disease that causes the failure of coronary circulation to supply adequate circulation to the cardiac muscles and surrounding tissues. Cardiovascular disease includes any of a number of specific diseases that affect the heart itself and/or the blood vessel system, especially the myocardial tissue, as well as veins and arteries leading to and from the heart. For example, CVD may include, but is not limited to, acute coronary syndromes, arrhythmia, atherosclerosis, heart failure, myocardial infarction, neointimal hyperplasia, pulmonary hypertension, stroke, and/or valvular disease. CVD may be diagnosed by any of a variety of methods known in the art. For example, such methods may include assessing a subject for dyspnea, orthopnea, paroxysmal nocturnal dyspnea, claudication, angina, chest pain, which may present as any of a number of symptoms known in the art, such as exercise intolerance, edema, palpitations, faintness, loss of consciousness, and/or cough.

Atherosclerosis is a heart disease in which an artery wall thickens as the result of a build-up of fatty materials such as cholesterol. It is a syndrome affecting arterial blood vessels, a chronic inflammatory response in the walls of arteries, in large part due to the accumulation of macrophage white blood cells and promoted by low-density lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries.

Methods of the invention contemplate the use of patient-derived samples that are used in assays or tests in order to obtain particular information. Samples generally refer to biological samples isolated from a subject and can include, without limitation, whole blood, serum, plasma, blood cells, endothelial cells, tissue biopsies, lymphatic fluid, ascites fluid, interstitital fluid (also known as "extracellular fluid" and encompasses the fluid found in spaces between cells, including, inter alia, gingival crevicular fluid), bone marrow, cerebrospinal fluid (CSF), saliva, mucous, sputum, sweat, urine, or any other secretion, excretion, or other bodily fluids. In preferred embodiments, the patient sample is a blood sample, which can include whole blood or any fraction thereof, including blood cells, serum and plasma.

Methods of the invention are used to determine compliance with a treatment used to improve total cholesterol levels, LDL cholesterol levels, HDL cholesterol levels, or combinations thereof. In certain embodiments, methods of the invention provide for administering the same or a different therapy to improve total cholesterol levels, LDL cholesterol levels, HDL cholesterol levels, or combinations thereof. The aim of therapy is to achieve cholesterol levels (total, LDL, HDL) that are normal or have a lower risk of heart disease. Ideal guidelines for total cholesterol levels, LDL cholesterol levels, and HDL cholesterol levels are described hereinafter.

According to certain embodiments, methods of the invention are used to determine compliance with a treatment to lower density lipoprotein (LDL) cholesterol (LDL-C), which is associated with increased heart risk. The following are typical guidelines for LDL cholesterol levels. LDL cholesterol below 70 mg/dL (1.8 mmol/L) is ideal for people at very high risks of heart disease. LDL cholesterol below 100 mg/dL (2.6 mmol/L) is ideal for people at risk of heart disease and normal patient populations. LDL cholesterol levels between 100 mg/dL and 129 mg/dL (2.6-3.3 mmol/L) is near ideal. LDL cholesterol levels between 130 mg/dL and 159 mg/dL (3.4-4.1 mmol/L) is borderline high. LDL cholesterol levels between 160 mg/dL and 189 mg/dL (4.1-4.9 mmol/L) is high. LDL cholesterol levels between 190 mg/dL and above (above 4.9 mmol/L) is very high.

In certain embodiments, methods of the invention are used to determine compliance with a treatment to increase high density lipoprotein (HDL) cholesterol (HDL-C). HDL-C can protect against atherosclerosis in several ways. The most cited HDL-C function to protect against atherosclerosis is its participation in reverse cholesterol transport. During this process, HDL-C removes cholesterol from macrophages in the vessel wall, preventing the transformation of macrophages into foam cells, eventually preventing the build-up of fatty streaks and plaque in the vessel wall. HDL-C also acts as an anti-oxidant and anti-inflammatory agent, which prevents oxidation of LDL and reduces cholesterol build-up caused by oxidized LDL. The following are typical guidelines for HDL cholesterol levels. HDL cholesterol levels below 40 mg/dL (men) and below 50 mg/dl (women) is considered poor. HDL cholesterol levels between 40-49 mg/dL (men) and 50-59 mg/dL (women) is intermediate. HDL cholesterol levels above 60 mg/dL is ideal.

In addition, methods of the invention may be used to determine compliance with a treatment to lower total cholesterol. The following are typical guidelines for total cholesterol levels. Total cholesterol below 200 mg/dL is ideal/normal. Total cholesterol ranging between 200 and 239 mg/dL is borderline high for risk of heart disease. Total cholesterol above 240 mg/dL is high for risk of heart disease.

A key step for determining a patient's compliance with a prescribed course of treatment is analyzing one or more cholesterol biomarkers of the patient prior to prescribing and having the patient undergo the prescribed course of treatment. The prescribed course of treatment may be an initial course of treatment or different course treatment (e.g. changing a drug dosage or drug type). Preferably, the one or more cholesterol markers are sterol markers. Sterol markers include cholesterol absorption markers, cholesterol production markers, or combinations thereof. Cholesterol absorption markers allow one to determine a level of cholesterol, received through the diet that is absorbed by the small intestine. Cholesterol production markers allow one to determine how much cholesterol cells are synthesizing.

An individual's ability to produce and absorb cholesterol is an important factor contributing the individual's total cholesterol and LDL cholesterol. This is because all LDL-C present in the body is the result of production of cholesterol from the liver and absorption of cholesterol from the diet. By analyzing a patient's cholesterol production and/or absorption markers, one is able to determine how the patient absorbs and absorbs cholesterol. Some people synthesize cholesterol more than they absorb cholesterol (over-producers), while others absorb more cholesterol than they synthesize (over-absorber).

Knowing how an individual produces and absorbs cholesterol allows one to determine and prescribe the most appropriate course of treatment, either at the initiation of initial therapy or at a change in current therapy, because each mechanism can be controlled by a different cholesterol lowering drug. For example, an over-producer will achieve lower cholesterol levels if prescribed a drug that inhibits cholesterol production. Likewise, an over-absorber will achieve lower cholesterol levels if prescribed a drug that inhibits cholesterol absorption. Thus, prescribing a course of treatment directed towards a patient's cholesterol absorption or production markers allows one to reliably predict how a compliant patient will respond to the prescribed course of treatment.

Cholesterol production markers include, for example, lathosterol and desmosterol. About eighty percent of synthesized cholesterol goes through lathosterol, while about 20% of synthesized cholesterol goes through desmosterol. People who overproduce cholesterol have elevated levels of lathosterol and desmosterol normalized to total blood cholesterol levels. As a result, levels of lathosterol and desmosterol can be used as markers to determine whether an individual is an overproducer of cholesterol.

Cholesterol absorption markers include, for example, beta-sitosterol and campesterol. These plant sterols are direct measures of cholesterol absorption. Individuals who over-absorb cholesterol in the intestine have elevated levels of these markers. Decreased values, which reflect low cholesterol absorption, are optimal.

The following tables categorize optimal, borderline, high, and very high levels of cholesterol absorption markers and cholesterol production markers for men and women.

TABLE 1

| | Women | | | |
|---|---|---|---|---|
| | Production Markers | | Absorption Markers | |
| | Lathosterol | Desmosterol | Beta-sitosterol | Campesterol |
| Optimal | <130 | <70 | <130 | <180 |
| Borderline | 130-150 | 70-80 | 130-160 | 180-300 |
| High | >150 | >80 | >250 | >400 |
| Very High | >200 | >150 | >250 | >400 |

(Sterol values in moles × $10^2$ mol of cholesterol)

TABLE 2

| | Men | | | |
|---|---|---|---|---|
| | Production Markers | | Absorption Markers | |
| | Lathosterol | Desmosterol | Beta-sitosterol | Campesterol |
| Optimal | <120 | <70 | <150 | <200 |
| Borderline | 120-135 | 70-75 | 150-160 | 200-220 |
| High | >135 | >75 | >160 | >300 |
| Very High | >200 | >150 | >250 | >400 |

(Sterol values in moles × $10^2$ mol of cholesterol)

Certain aspects of the invention involve conducting an assay to determine a level of a patient's cholesterol production marker, cholesterol absorption marker, or both. From the assay, method of the invention provide for determining whether the patient is an over-absorber or an over-producer of cholesterol using the cholesterol production markers, the cholesterol absorption markers, or both, which are outlined in Tables 1 and 2. Whether a person is an overproducer or an overabsorber are important factors in determining a course of treatment for lowering cholesterol. Individuals who are overproducers of cholesterol benefit from a drug that inhibits cholesterol production (such as a statin). Individuals who are over-absorbers of cholesterol benefit from a drug that inhibits cholesterol absorption (such as an ezetimibe). This sterol analysis is important because it provides a guideline for a physician to prescribe a course of treatment best suited for the individual based on the sterols. In certain embodiments, high or very high levels of cholesterol absorption markers are indicative that a patient is an over-absorber and would benefit from a therapy to inhibit cholesterol absorption. In other embodiments, high or very high levels of cholesterol production markers are indicative that a patient is an over-producer and would benefit from a therapy to inhibit cholesterol production.

According to certain embodiments, methods of the invention provide for balancing the cholesterol production markers against the cholesterol absorption markers to determine whether the patient is an over-absorber or over-producer. In these embodiments, an assay is conducted to determine levels of one or more cholesterol production markers and an assay is conducted to determine one or more cholesterol production markers of an individual. The assay of the cholesterol production markers may be the same or different from the assay for the cholesterol absorption markers. The cholesterol production marker levels are then compared against the cholesterol absorption marker levels. This comparison step allows one to determine whether it is the amount of cholesterol produced by the body or the amount of cholesterol absorb by the intestine that is contributing to total blood cholesterol and LDL cholesterol levels.

In certain embodiments, methods of the invention provide for assigning a weighted value to each risk category (optimal, borderline, high, very high) for each cholesterol absorption marker and each cholesterol production marker. A weighted value for cholesterol production markers may be compare to a weighted value for cholesterol absorption markers to determine whether an individual is an overproducer or over-absorber. The weighted value may be scaled in any manner including and not limited to assigning a positive or negative integer to reflect the significance or severity of the risk category towards increasing cholesterol. The weighted value for each risk category for each marker may also take into consideration the percent contribution (n) that marker has towards the patient's cholesterol levels. For example, lathosterol contributes to 80% of synthesized cholesterol and desmosterol contributes to only 20% of synthesized cholesterol. The weighted values of the cholesterol absorption markers can be compared to the weighted values of the cholesterol production markers to determine which one is contributing more to the cholesterol. For example, Table 3 shows a simplified method for assigning weighted values to cholesterol production and cholesterol absorption markers for men. While weighted values of Table 3 are shown for illustrative purposes, any method for quantitatively and qualitatively comparing the production markers to the absorption markers may be used. It is also understood that the same concept may apply to those markers for women in Table 2.

TABLE 3

| | Men | | | |
|---|---|---|---|---|
| | Production Markers | | Absorption Markers | |
| | Lathosterol | Desmosterol | Beta-sitosterol | Campesterol |
| Optimal | <120 Weighted Value: 1 * n | <70 Weighted value: 1 * n | <150 Weighted Value: −1 * n | <200 Weighted Value: −1 * n |
| Border-line | 120-135 Weighted Value: 2 * n | 70-75 Weighted Value: 2 * n | 150-160 Weighted Value: −2 * n | 200-220 Weighted Value: −2 * n |
| High | >135 Weighted Value: 3 * n | >75 Weighted Value: 3 * n | >160 Weighted Value: −3 * n | >300 Weighted Value: −3 * n |
| Very High | >200 Weighted Value: 4 * n | >150 Weighted Value: 4 * n | >250 Weighted Value: −4 * n | >400 Weighted Value: −4 * n |

As shown in Table 3, each category for each biomarker is assigned a weighted value that is multiplied by that markers contribution to either cholesterol production or cholesterol absorption. Using the weighted values, one can balance the cholesterol absorption values against the cholesterol production values. The following are non-limiting guidelines for balancing cholesterol production with cholesterol absorption. When the sum of cholesterol absorption and cholesterol production values totals −1, 0, or 1, the individual is producing cholesterol at a substantially similar level as the individual is absorbing cholesterol. As a result, the individual is classified as a balanced producer. When the sum of the cholesterol absorption and cholesterol production values is less than −1, the individual is over-absorbing cholesterol and is classified as an over-absorber. When the sum of the cholesterol absorption and cholesterol production values is greater than 1, the individual is over-producing cholesterol and is classified as an over-absorber.

Once an individual is established as an over-producer, a balanced producer, or an over-absorber, methods of the invention provide for prescribing/administering a course of treatment designed to lower the cholesterol of the patient. For balanced producers, the individual may be prescribed a cholesterol production inhibiting drug alone or in combination with an ezetimibe in order to reduce cholesterol. For over-producers, the individual may be prescribed a cholesterol production inhibiting drug. For over-absorbers, the individual may be prescribed a cholesterol absorption inhibiting drug.

In some instances, a patient may already be on a cholesterol reducing therapy. In such instances, the cholesterol balance test can be utilized to provide a course of treatment to enhance the current cholesterol reducing therapy. For example, balancing the cholesterol production makers and cholesterol absorption makers of a patient already undergoing a statin therapy may show that the patient is an over-absorber of cholesterol. This is because the statin therapy while decreasing the cholesterol production markers also increases the cholesterol absorption markers. In this example, the course of treatment may be to add a cholesterol absorption inhibiting drug to the statin therapy in order to assist in decreasing cholesterol. The benefits of combining cholesterol absorption inhibiting drugs to a cholesterol production inhibiting therapy are described in more detail in the Example 1 herein. See also Thongtang et al., "Effects of ezetimibe added to statin therapy on markers of cholesterol absorption and synthesis and LDL-C lowering in hyperlipidemic patients," Atherosclerosis, Volume 225, Issue 2, December 2012, Pages 388-396, the entirety of which is incorporated by reference.

In addition, the degree to which an individual is classified as an over-producer or an under-producer can be used to determine, for example, the dosage and type of drug the patient should be administered. For example, if the cholesterol balancing test indicates that high risk levels of cholesterol production markers are responsible for elevated total cholesterol (e.g. when there is minimal to no levels of cholesterol absorption markers), then a high statin dosage and/or a medium to high potency statin may be appropriate. In another example, if the cholesterol balancing test indicates that the patient is a balanced producer, yet still has high cholesterol, the patient may benefit from a low or medium potency statin along with ezetimibe treatment.

The cholesterol production inhibiting drug is typically a statin. A statin is class of drugs used to lower cholesterol levels by inhibiting the enzyme HMG-CoA reductase, which plays a central role in the production of cholesterol in the liver. Statins may include but are not limited to Advicor® (niacin extended-release/lovastatin), Altoprev® (lovastatin extended-release), Caduet® (amlodipine and atorvastatin), Crestor® (rosuvastatin), Lescol® (fluvastatin), Lescol XL (fluvastatin extended-release), Lipitor® (atorvastatin), Livalo® (pitavastatin), Mevacor® (lovastatin), Pravachol® (pravastatin), Simcor® (niacin extended-release/simvastatin), Vytorin® (ezetimibe/simvastatin), Zocor® (simvastatin), or generic atorvastatin, lovastatin, pravastatin, or simvastatin. Typically, statin dosage is the amount of a statin required to reduce LDL-C to target level relative to an untreated patient. Statin dosage may depend upon the manner of administration, the age, body weight, and general health of the subject. Additionally, statin dosage may vary depending upon which statin is being administered. For example, a typical statin dosage range for atorvastatin, pravastatin, lovastatin, fluvastatin and simvastatin is from about 10 mg to about 80 mg. Low potency statins are predicted at lowering LDL-C by ~20-30%, and may include the following stains and dosages: simvastatin ≤10 mg/day, lovastatin ≤20 mg/day, pravastatin ≤20 mg/day, and fluvastatin ≤40 mg/day. The medium potency statins are predicted at lowering LDL-C by ~31-45%, and may include the following statins and dosages: simvastatin >10 to ≤40 mg/day, atorvastatin ≤20 mg/day, lovastatin >20 to 80 mg/day, pravastatin >20 to 80 mg/day, and fluvastatin >40 to 80 mg/day. The high potency statins are predicted at lowering LDL-C by ~46-55%, and may include the following statins and dosages: simvastatin >40 to 80 mg/day, and atorvastatin >20 to 80 mg/day.

Drugs that inhibit cholesterol absorption that are suitable for use in methods of the invention include the drug ezetimibe, candicidin and other polyene macrolides, or bile acid sequestering anionic exchange resins such as Cholestyramine® and Colestipol®. Preferably, the cholesterol absorption drug is ezetimibe. Ezetimibe's mode of action involves the inhibition of cholesterol absorption and resorption in the intestinal tract. This mechanism of action also involves the increased excretions of cholesterol and its intestinal generated metabolites with the feces. This effect of ezetimibe results in lowered body cholesterol levels, increased cholesterol synthesis, and decreased triglyceride synthesis. The increased cholesterol synthesis initially provides for the maintenance of cholesterol levels in the circulation, levels that eventually decline as the inhibition of cholesterol absorption and resorption continues. The overall effect of drug action is the lowering of cholesterol levels in the circulation and tissues of the body. Ezetimibe is typically delivered n 10 mg/day dosages, when used alone or in combination with a statin therapy.

By establishing an individual as an over-producer, a balanced producer, or an over-producer using cholesterol absorption and cholesterol production markers, one can reliably predict how a compliant individual will respond to the prescribed treatment. For example, an over-producer of cholesterol on a statin therapy should achieve lower cholesterol when compliant with the statin therapy. An over-absorber of cholesterol on an ezetimibe therapy should achieve lower cholesterol when compliant with the ezetimibe therapy. A balanced producer on a statin therapy or a combined statin and ezetimibe therapy should achieve lower cholesterol when compliant with either therapy.

According to methods of the invention, the ability to predict how a compliant patient will respond to a course of treatment is used to determine whether the patient is complying with the course of treatment. In order to accomplish this, methods of the invention provide for monitoring/determining an actual change in a patient's cholesterol level in order to determine whether the patient is complying with the course of treatment. In certain embodiments, an assay is conducted to determine a level of cholesterol from a sample of a patient undergoing the course of treatment. The sample level of cholesterol is then compared to a reference level of cholesterol. Ideally, the patient is undergoing the course of treatment for a period of time after the reference level is obtained. The period of time should be long enough for the course of treatment to have an effect on the patient's cholesterol level. The reference level of cholesterol may be the patient's cholesterol level prior to the start of the initial treatment or prior to the initiation of a different treatment (such as an increased dosage or different drug type). If the individual's cholesterol lowers as predicted for compliancy, the patient is classified as compliant. If the individual's cholesterol remains substantially unchanged (substantially zero change) or increases, the patient is classified as non-compliant.

As an alternative to monitoring cholesterol levels or in conjunction with monitoring cholesterol levels, an individual's cholesterol biomarker levels may be monitored to determine whether a patient is compliant with treatment. For example, an over-producer of cholesterol on a statin therapy should achieve lower levels of cholesterol production markers. In another example, an over-absorber of cholesterol on an ezetimibe therapy should achieve lower levels of cholesterol absorption biomarkers when compliant with the ezetimibe therapy.

Methods of the invention provide for monitoring an actual change in a patient's cholesterol markers in order to determine whether the patient is complying with statin therapy. In certain embodiments, a sample level of one or more cholesterol markers is obtained from a patient undergoing a statin therapy. The sample level of one or more cholesterol markers is then compared to a reference level of cholesterol markers. The reference level of one or more cholesterol markers may be the patient's level of cholesterol markers prior to initiation of statin therapy, the patient's level of cholesterol markers on a different statin therapy (e.g. lower dose or different cholesterol lowering drug), or known, typically cholesterol marker levels from a patient reference population (e.g. patient population with similar attributes as the patient). Ideally, the patient is undergoing the course of treatment for a period of time after the reference level is obtained. The period of time should be long enough for the course of treatment to have an effect on the patient's cholesterol level. If the individual's level of a cholesterol biomarker lowers as predicted for compliancy, the patient is classified as compliant. If the individual's level of cholesterol biomarker remains substantially unchanged (substantially zero change) or increases, the patient is classified as non-compliant.

By identifying non-compliance, the provider can confront the individual with the evidence of non-compliance and identify the cause of the patient's non-compliance. In addition, the healthcare provider is able to administer the appropriate drugs in order to assist the patient in efficiently reaching his LDL-C goals. For example, the provider may administer/prescribe the same course of treatment with a better plan for assisting the patient to remain compliant. In another example, if the non-compliance is due to the patient's side effects on the course of treatment, the provider may prescribe an alternative therapy that has the same cholesterol lowering benefits without the side effects or the provider may prescribe additional medication that reduces the side effects of the current course of treatment.

Additionally, if the patient is found compliant, the provider is able to objectively determine the next step of treatment because the provider no longer has to rely on patient's self-reporting for compliance. If the compliant, over-producer patient's cholesterol levels are still in a high risk category, the doctor may, for example, increase the statin dosage. If the compliant, over-absorber patient's cholesterol levels are still in a high risk category, the doctor may, for example, provide a different diet plan with the ezetimibe treatment in an effort to achieve cholesterol lowering goals.

Any assay for measuring cholesterol may be used in accordance with methods of the invention. The assay may be to determine a level of total cholesterol, HDL cholesterol, or LDL cholesterol. Rifai et al., Handbook of Lipoprotein Testing (Amer. Assoc. for Clinical Chemistry, 2000) provides a general outline of various assays for measuring total cholesterol, HDL cholesterol, and LDL cholesterol.

In one embodiment, a Liebermann-Burchard (L-B) assay is used to measure total cholesterol in blood. This is an absorbance-based assay. First, the L-B reaction reagent is prepared, which consists of solution of 30% glacial acetic acid, 60% acetic anhydride, and 10% sulphuric acid. Secondly, 5 ml of this L-B reagent is then added to 0.2 ml of a sample derived from blood plasma, which are mixed together and then allowed to stand for 20 minutes. The L-B reaction is usually carried out on a sample comprising cholesterol that has been extracted from plasma into an organic solvent. The products of the L-B reaction are two colored products. The absorbance of the products, the concentration of which are related to the concentration of cholesterol, is then measured using a spectrophotometer. The total concentration of cholesterol may be determined from a calibration curve of absorbance against cholesterol concentration, using cholesterol standards (Burke et ah, Clin. Chem. 20(7), 794-801 (1974)). Total cholesterol can also be measured using an isotope dilution-mass spectrometric method, which is described in Schaffer, R., et al. "Comparison of two isotope dilution/mass spectrometric methods for determination of total serum cholesterol." Clinical chemistry 28.1 (1982): 5-8.

In another example, an enzymatic method is used for the determination of total cholesterol. In these methods, free cholesterol and esterified cholesterol are subjected to chemical or enzymatic saponification to convert the latter cholesterol to free cholesterol. All free cholesterols are allowed to interact with a cholesterol oxidase, and the formed hydrogen peroxide, cholestenone, or consumed oxygen is measured. See Clin. Chem., 20, 470, 1974; U.S. Pat. Nos. 3,925,164 and 4,212,938). These formed products are used as a measure of cholesterol. In some methods, the formed hydrogen peroxide is allowed to react with a peroxides and a color-producing reagent. The resulting colored substance is used as a measure of total cholesterol. Alternatively, a cholesterol dehydrogenase and NAD or NADP as a coenzyme are used can be used to interact with the free cholesterol to form cholestenone or the reduced type NAD (after referred to as NADH) or reduced type NADP (after referred to as NADPH). (U.S. Pat. No. 4,181,575; FRG Patent Laid-open No. 3,032,377 and Japanese Patent Laid-open No. 89, 200/1983). These formed products are used as a measure of total cholesterol.

Any assay for measuring LDL cholesterol may be used in accordance with methods of the invention. A common approach for measuring LDL cholesterol is the Friedewald calculation method, which estimates LDL-C from measurements of total cholesterol, triglycerides, and HDL-cholesterol. Other approaches involve direct measurement of LDL cholesterol. For example, LDL cholesterol may be measured using ultracentrifugation methods, electrophoresis methods, precipitation methods, methods that use polyethylene-glycol modified enzymes, methods that use synthetic polymers, immunological separation methods, and catalase reagent methods.

Ultracentrifugation for measuring LDL cholesterol separates lipoproteins based on their differing hydrated densities, which are adjusted by adding salts such as NaBr or KBr. Particularly, the proportion of lipid associated with the proteins for any one particular lipoprotein adds to the buoyancy of the lipoprotein complex, which allows it to be separated. Preparative fractionations are achieved by subjecting serum or plasma to ultracentrifugation at the native non-protein solute density, which floats TG-rich BLDL and chylomicrons. Those can be recovered using tube slicing or aspiration. The bottom fraction contains the LDL and HDL, which can be re-centrifuged, after adding salt, to float LDL.

For measuring of LDL-C by electrophoresis, lipoproteins may be separated using a variety of electrophoric media, such as paper, agarose gel, cellulose acetate, and polyacrylamide with one or more buffers. A preferred electrophoresis separation and immune-detection technique is described in co-owned and co-assigned U.S. patent application Ser. No. 12/567,737. A common technique uses agarose gels to separate lipoproteins followed by precipitation with polyanions and densitometric scanning. This technique can be approved by the introduction of enzymatic cholesterol determination using cholesterol esterase, cholesterol dehydrogenase, and nitroblue tetrazolium chloride dye. An alternative technique uses agarose gel modified by addition of a cation such as magnesium, which slows migration of β and pre-β lipoproteins, producing a distinct additional band between pre-β and α lipoproteins, demonstrated to be Lp(a) by immunofixation. Addition of urea to the gel allowed simultaneous quantification of the β, pre-β, and α fractions as well as Lp(a)-cholesterol with the mobility of Lp(a) independent of apo(a) size polymorphisms.

Another technique for direct measurement of LDL cholesterol is an immunoseparation method, known as Direct LDL from Genzyme Diagnostics and Signma Diagnostics. This technique uses a reagent that contained polyclonal (goat) antibodies to human apo A-I m and apo E bound to polystyrene latex beads and that was designed to remove chylomicrons, HDL, VLDL, and IDL particles, allowing direct determination of LDL-C. In yet another technique for direct measurement of LDL cholesterol involves magnetic precipitation, such as a technique used by Reference Diagnostics. The magnetic precipitation technique used heparin-coated beads at pH 5.1 to remove LDL from serum, leaving HDL and VLDL remaining in the solution.

In addition, homogenous assays for measuring LDL cholesterol may be used. One homogeneous method for determining LDL-C is disclosed in U.S. Pat. No. 5,888,827 (Kayahara, Sugiuchi, et al.; assigned to Kyowa Medex Co., Japan). The '827 patent describes a two-stage liquid phase reaction to quantify LDL-C concentration in a fluid sample. In the first step, the sample containing LDL-C is placed in a first reagent that includes trimethyl beta-cyclodextrin as a sugar compound, polyoxyethylene monolaurate as a protein solubilizing agent, EMSE (N-ethyl-N-(3-methylphenyl)-N', succinylethylenediamene) and Tris buffer. The reaction mixture is then heated to 37° C., and after 5 minutes the absorbance is read. A second reagent including cholesterol esterase, cholesterol oxidase, peroxidase, 4-aminoantipyrine and Tris buffer is then added and after another 5 minutes the absorbance is again measured at the same wavelength. LDL-C is then calculated by separately subjecting a standard solution of cholesterol to the same procedure and comparing the respective absorbance values.

Another two-stage homogeneous assay is disclosed in U.S. Pat. No. 6,194,164 (Matsui et al.; assigned to Denke Seiken, Ltd. Japan). In the first stage, HDL-C, VLDL-C and Chylomicron-C in the test sample are eliminated and, in the second step, the cholesterol remaining in the test sample (viz., LDL) is quantified. In the first step, cholesterol esterase and cholesterol oxidase act on the test sample in the presence of a surfactant that acts on lipoproteins other than LDL-C ("non-LDLs"). The hydrogen peroxide thereby generated is decomposed to water and oxygen by catalase. Alternatively, a phenol-based or aniline-based hydrogen donor is reacted with the hydrogen peroxide to convert it to a colorless compound. Preferred surfactants that act on the non-LDLs include polyoxyethylene laurl ether, polyoxyethylene cetyl ether, polyoxyethylene oleyl ether, polyoxyethylene higher alcohol ether, and the like. In the second reaction disclosed in the '164 patent, cholesterol remaining in the test sample, which should theoretically contain only LDL-C, is quantified. The second step may be carried out by adding a surfactant that acts on at least LDL and quantifying the resulting hydrogen peroxide by the action of the cholesterol esterase and the cholesterol oxidase added in the first step.

A homogeneous assay for measuring LDL-C in serum was disclosed by H. Sugiuchi et al., Clinical Chemistry 44:3 522-531 (1998). This disclosure shows a correlation between the use of a combination of triblock copolymer and alpha-cyclodextrin sulfate and the selective enzymatic reaction of LDL-C when both LDLs and non-LDLs are contacted with the combination in a liquid assay system.

In a homogenous assay from Diiachi Pure Chemicals Company, a3-µL serum sample is incubated with 300 µL of reagent 1 for 5 min at 37° C. Reagent 1 contains ascorbic acid, oxidase, 4-aminoantipyrene, peroxidase, cholesterol oxidase, cholesterol esterase, buffer (pH 6.3), and a detergent, which solubilizes all non-LDL lipoproteins. The cholesterol reacts with cholesterol esterase and cholesterol oxidase, generating hydrogen peroxide, which is consumed by a peroxidase in the presence of 4-aminoantipyrine with no color generation. Reagent 2 (100 µL) is then added, which contains N,N-bis-(4-sulfobutyl)-m-toluidine disodium salt, buffer (pH 6.3), and a specific detergent, which specifically releases cholesterol from LDL particles. An enzymatic reaction similar to that described above occurs except that the hydrogen peroxide reacts with N,N'-bis-(4-sulfobutyl)-m-toluidine disodium salt to generate a colored product [measured at 546 (main) and 660 (subsidiary) nm] that is proportional to LDL-C.

A homogeneous LDL-C assay from International Reagents Corporation uses 5 µL of serum and 180 µL of reagent 1 with incubation, Calixarene, a detergent, converts LDL to a soluble complex, Cholesterol esters of HDL-C and VLDL-C are preferentially hydrolyzed by a cholesterol esterase (Chromobacterium); cholesterol oxidase and hydrazine then convert the accessible cholesterol to cholestenone hydrazone. In a second step, 60 µL of reagent 2 (deoxycholate) is added, breaking up the LDL-calixarene complex and allowing, LDL-C to react with the esterase, a dehydrogenase, and β-NAD to yield cholestenone and β-NADH; the latter is measured spectrophotometrically.

Other assays for measuring LDL cholesterol include a solubilization LDL-C assay (SOL; Kyowa Medex), a surfactant LDL-C assay (SUR; Daiichi), a protecting reagent assay (PRO; Wako), a catalase LDL-C assay (CAT; Denka Seiken), and a calixarene LDL-C assay (CAL; International Reagents Corporation). Each of these assays are described in more detail in Nauck et al., Clinical Chemistry February 2002 vol. 48 no. 2 236-254.

Any assay for measuring HDL cholesterol may be used in accordance with methods of the invention. The general techniques for quantifying levels of HDL cholesterol are similar to and often the same techniques for quantifying levels of LDL cholesterol. For example, HDL cholesterol may also be measured using ultracentrifugation methods, electrophoresis methods, precipitation methods, methods that use polyethylene-glycol modified enzymes, methods that use synthetic polymers, immunological separation methods, and catalase reagent methods. These techniques and more are described in more detail in Warnick et al., Clinical Chemistry September 2001 vol. 47 no. 9 1579-1596.

Generally, ultracentrifugation techniques for measuring HDL-C separate lipoproteins based on their differing hydrated densities. Particularly, the proportion of lipid associated with the proteins for any one particular lipoprotein adds to the buoyancy of the lipoprotein complex, which allows it to be separated. This allows HDL-C to be separated from LDL-C, etc. For measuring HDL-C by electrophoresis, lipoproteins may be separated using a variety of electrophoric media, such as paper, agarose gel, cellulose acetate, and polyacrylamide with one or more buffers. A preferred electrophoresis separation and immune-detection technique is described in co-owned and co-assigned U.S. patent application Ser. No. 12/567,737. Lipoproteins separated by electrophoresis can be identified using immuno-detection techniques.

Precipitation and homogenous assays for separating HDL-C typically involve addition of two or more reagents to a sample, with incubation periods after addition of the reagents, followed by a measurement step, e.g. by colorimetric development or by UV/Vis analysis. For example, precipitation techniques for separating HDL-C involve the reaction of a precipitation reagent with low density lipoproteins (LDL), very low density lipoproteins (VLDL) and chylomicrons (CM) in order to form an aggregate of these components. The aggregate was then removed from the reaction vessel, for example by centrifugation, leaving an HDL-containing sample ready for analysis. Separation of the precipitate was essential in order that the precipitate did not interfere with the UV/Vis or colorimetric analysis techniques used. Homogenous assays for separating HDL particles are similar to precipitation assays, but typically do not require separation of precipitated lipoproteins. Instead, a clearing reagent is added to dissolve the precipitate after reaction with HDL-cholesterol is completed. In this way, the LDL, VLDL and CM are blocked ensuring selective reaction with HDL-cholesterol, but are cleared prior to carrying out the UV/Vis analysis. Alternatively, specific reaction conditions such as high dilution, or specific precipitation reagents, are used to ensure minimum interference with the analysis technique.

In certain embodiments, plasma total cholesterol (total C), high-density lipoprotein cholesterol (HDL-C), and triglycerides (TG) were analyzed using standardized methods at the central laboratory of the trial (PPD Global Central Labs, Highland Heights, Ky., USA). LDL-C was calculated using the Friedewald formula. Friedewald W T, Levy R I, Fredrickson D S. Estimation of the concentration of low-density lipoprotein cholesterol in plasma, without use of the preparative ultracentrifuge. Clin Chem 1972; 18:499-502. Non-HDL-C was calculated by subtracting HDL-C from total C.

Methods of the invention also utilize one or more assays in order to determine a level of one or more cholesterol absorption markers and to determine a level of one or more cholesterol production markers. The one or more assays to determine a level of one or more cholesterol absorption markers may be the same or different. The one or more assays to determine a level of one or more cholesterol production markers may be the same or different. In addition, the assay used to determine a level of cholesterol production marker may be the same or different.

Levels of cholesterol production markers and levels of cholesterol absorption markers can be determined using any assay known in the art. These biomarkers may readily be isolated and/or quantified by methods known to those of skill in the art, including, but not limited to, methods utilizing: mass spectrometry (MS), high performance liquid chromatography (HPLC), isocratic HPLC, gradient HPLC, normal phase chromatography, reverse phase HPLC, size exclusion chromatography, ion exchange chromatography, capillary electrophoresis, microfluidics, chromatography, gas chromatography (GC), thin-layer chromatography (TLC), immobilized metal ion affinity chromatography (IMAC), affinity chromatography, immunoassays, and/or colorimetric assays. In certain embodiments, cholesterol production and absorption markers are determined by using gas chromatography techniques, gas chromatography mass spectrometry (GC-MS) techniques, and/or high performance liquid chromatography (HPLC) techniques.

Gas chromatography techniques generally involve sample preparation, derivatization, and gas chromatography analysis. Sample preparation involves sample weighing, an optional step of lipid extraction, addition of an internal standard, hydrolysis (acid and/or alkaline), extraction of unsaponifiables, and purification. Derivation involves converting the substance (sterols) to be analyzed into a more volatile derivative that can be used for gas chromatography analysis. A gas chromatograph uses a flow-through narrow tube known as the column, through which different chemical constituents of a sample pass in a gas stream (carrier gas, mobile phase) at different rates depending on their various chemical and physical properties and their interaction with a specific column filling, called the stationary phase. As the chemicals exit the end of the column, they are detected and identified electronically. The function of the stationary phase in the column is to separate different components, causing each one to exit the column at a different time (retention time). Other parameters that can be used to alter the order or time of retention are the carrier gas flow rate, column length and the temperature. In a GC analysis, a known volume of gaseous or liquid analyte is injected into the "entrance" (head) of the column, usually using a microsyringe (or, solid phase microextraction fibers, or a gas source switching system). As the carrier gas sweeps the analyte molecules through the column, this motion is inhibited by the adsorption of the analyte molecules either onto the column walls or onto packing materials in the column. The rate at which the molecules progress along the column depends on the strength of adsorption, which in turn depends on the type of molecule and on the stationary phase materials. Since each type of molecule has a different rate of progression, the various components of the analyte mixture are separated as they progress along the column and reach the end of the column at different times (retention time). A detector is used to monitor the outlet stream from the column; thus, the time at which each component reaches the outlet and the amount of that component can be determined. Generally, substances are identified (qualitatively) by the order in which they emerge (elute) from the column and by the retention time of the analyte in the column.

Gas chromatography-mass spectrometry (GC-MS) is a method that combines the features of gas-liquid chromatography and mass spectrometry to identify different substances within a test sample. The GC-MS includes two components the gas chromatograph and the mass spectrometer. The gas chromatograph utilizes a capillary column which depends on the column's dimensions (length, diameter, film thickness) as well as the phase properties. The difference in the chemical properties between different molecules in a mixture will separate the molecules as the sample travels the length of the column. The molecules are retained by the column and then elute (come off) from the column at different times (called the retention time), and this allows the mass spectrometer downstream to capture, ionize, accelerate, deflect, and detect the ionized molecules separately. The mass spectrometer does this by breaking each molecule into ionized fragments and detecting these fragments using their mass to charge ratio. The most common type of mass spectrometer (MS) associated with a gas chromatograph (GC) is the quadrupole mass spectrometer, sometimes referred to by the Hewlett-Packard (now Agilent) trade name "Mass Selective Detector" (MSD).

Another relatively common detector is the ion trap mass spectrometer. Other detectors may be encountered such as time of flight (TOF), tandem quadrupoles (MS-MS), or in the case of an ion trap MSn where n indicates the number mass spectrometry stages. When a second phase of mass fragmentation is added, for example using a second quadrupole in a quadrupole instrument, it is called tandem MS (MS/MS). MS/MS can sometimes be used to quantitate low levels of target compounds in the presence of a high sample matrix background. The first quadrupole (Q1) is connected with a collision cell (q2) and another quadrupole (Q3). Both quadrupoles can be used in scanning or static mode, depending on the type of MS/MS analysis being performed. Types of analysis include product ion scan, precursor ion scan, selected reaction monitoring (SRM) (sometimes referred to as multiple reaction monitoring (MRM)) and neutral loss scan. For example: When Q1 is in static mode (looking at one mass only as in SIM), and Q3 is in scanning mode, one obtains a so-called product ion spectrum (also called "daughter spectrum"). From this spectrum, one can select a prominent product ion which can be the product ion for the chosen precursor ion. The pair is called a "transition" and forms the basis for SRM. SRM is highly specific and virtually eliminates matrix background.

In other embodiments, levels of cholesterol absorption markers and cholesterol production markers are determined using high-performance liquid chromatography (HPLC). HPLC relies on pumps to pass a pressurized liquid and a sample mixture through a column filled with a sorbent, leading to the separation of the sample components. The active component of the column, the sorbent, is typically a granular material made of solid particles (e.g. silica, polymers, etc.), 2-50 micrometers in size. The components of the sample mixture are separated from each other due to their different degrees of interaction with the sorbent particles. The pressurized liquid is typically a mixture of solvents (e.g. water, acetonitrile and/or methanol) and is referred to as "mobile phase". Its composition and temperature plays a major role in the separation process by influencing the interactions taking place between sample components and sorbent. These interactions are physical in nature, such as hydrophobic (dispersive), dipole-dipole and ionic, most often a combination thereof. The schematic of an HPLC instrument typically includes a sampler, pumps, and a detector. The sampler brings the sample mixture into the mobile phase stream which carries it into the column. The pumps deliver the desired flow and composition of the mobile phase through the column. The detector generates a signal proportional to the amount of sample component emerging from the column, hence allowing for quantitative analysis of the sample components. A digital microprocessor and user software control the HPLC instrument and provide data analysis. Some models of mechanical pumps in a HPLC instrument can mix multiple solvents together in ratios changing in time, generating a composition gradient in the mobile phase. Various detectors are in common use, such as UV/Vis, photodiode array (PDA) or based on mass spectrometry. Most HPLC instruments also have a column oven that allows for adjusting the temperature the separation is performed at.

In addition, the following publications outline methods for measuring levels of cholesterol absorption and production biomarkers: Sudhop T, Lutjohann D, Kodal A, et al. "Inhibition of intestinal cholesterol absorption by ezetimibe in humans." Circulation 2002; 106:1943-8; Matthan N R, Giovanni A, Schaefer E J, Brown B G, Lichtenstein A H., "Impact of simvastatin, niacin, and/or antioxidants on cholesterol metabolism in CAD patients with low HDL." J Lipid Res. 2003; 44:800-806; Matthan N R, Raeini-Sarjaz M, Lichtenstein A H, Ausman L M, Jones P J., "Deuterium uptake and plasma cholesterol precursor levels correspond as methods for measurement of endogenous cholesterol synthesis in hypercholesterolemic women.", Lipids. 2000; 35:1037-1044; Grundy, Scott. "Plasma Non-Cholesterol Sterols as Indicators of Cholesterol Absorption." Journal of lipid research (2013); Tyburczy, Cynthia, et al. "Evaluation of low trans fat edible oils by attenuated total reflection-Fourier transform infrared spectroscopy and gas chromatography: a comparison of analytical approaches." Analytical and bioanalytical chemistry 404.3 (2012): 809-819; Luzón-Toro, Berta, Alberto Zafra-Gómez, and Oscar Ballesteros. "Gas chromatographic-mass spectrometric determination of brain levels of α-cholest-8-en-3β-ol (lathosterol)." Journal of Chromatography B 850.1 (2007): 177-182; Márk, L., and G. Paragh. "[Change in the cholesterol metabolism associated with the combined inhibition of synthesis and absorption]." Orvosi hetilap 148.14 (2007): 627; Lund, E., et al. "Determination of serum levels of unesterified lathosterol by isotope dilution-mass spectrometry." Scandinavian journal of clinical & laboratory investigation 49.2 (1989): 165-171; Goh, Edward H., Scott M. Colles, and Kimberly D. Otte. "HPLC analysis of desmosterol, 7-dehydrocholesterol, and cholesterol." Lipids 24.7 (1989): 652-655.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for determining a patient's compliance with a cholesterol lowering therapy and treating the patient, the method comprising:
   conducting a first assay to determine a level of a cholesterol absorption sterol and a level of a cholesterol production sterol in a first sample obtained from a patient prior to undergoing a cholesterol lowering therapy;

comparing the level of the cholesterol absorption sterol against the level of the cholesterol production sterol to classify the patient as a balanced producer, an over producer, or an over-absorber of cholesterol;

conducting a second assay to determine a cholesterol level in a second sample obtained from the patient after the patient has started undergoing the cholesterol lowering therapy;

identifying the patient as non-compliant with the cholesterol lowering therapy when the patient's cholesterol level has not decreased as expected compared to a prior cholesterol level taken from the patent before undergoing the cholesterol lowering therapy and given the patient's classification; and administering an alternative therapy to the patient in response to identifying the patient as non-compliant with the cholesterol lowering therapy.

2. The method of claim 1, wherein the first and second samples are blood samples.

3. The method of claim 1, wherein the cholesterol absorption sterol is selected from the group consisting of campesterol, beta-sitosterol, and a combination thereof.

4. The method of claim 1, wherein the cholesterol production sterol is selected from the group consisting of lathosterol, desmosterol, and a combination thereof.

5. The method of claim 1, wherein a drug administered in the cholesterol lowering therapy comprises a drug that inhibits cholesterol production.

6. The method of claim 5, wherein the drug that inhibits cholesterol production is a statin.

7. The method of claim 1, wherein a drug administered in the cholesterol lowering therapy comprises a drug that inhibits cholesterol absorption.

8. The method of claim 7, wherein the drug that inhibits cholesterol absorption is an ezetimibe.

9. The method of claim 1, wherein the cholesterol level is a level of LDL cholesterol.

\* \* \* \* \*

UNITED STATES PATENT AND TRADEMARK OFFICE
CERTIFICATE OF CORRECTION

PATENT NO.         : 9,828,624 B2
APPLICATION NO.    : 13/949847
DATED              : November 28, 2017
INVENTOR(S)        : Ernst J. Schaefer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 113 days.

Signed and Sealed this

Twenty-fifth Day of September, 2018

Andrei Iancu
*Director of the United States Patent and Trademark Office*